United States Patent [19]
Watt

[11] 3,949,611
[45] Apr. 13, 1976

[54] SAMPLE COLLECTING SYSTEM
[76] Inventor: Donald M. Watt, 420 Bourke St., Apt. 1E, Dorval, Quebec, Canada
[22] Filed: Jan. 20, 1975
[21] Appl. No.: 542,273

[52] U.S. Cl. ............................................. 73/421 B
[51] Int. Cl.² .......................................... G01N 1/14
[58] Field of Search ......... 73/422 R, 422 TC, 425.6, 73/421 B

[56] References Cited
UNITED STATES PATENTS

| 3,587,670 | 6/1971 | Brailsford | 73/421 B |
| 3,719,081 | 3/1973 | Lynn et al. | 73/422 R |

FOREIGN PATENTS OR APPLICATIONS

| 720,161 | 12/1954 | United Kingdom | 73/421 B |

Primary Examiner—James J. Gill
Assistant Examiner—Anthony V. Ciarlante

[57] ABSTRACT

A sample collecting system comprising a main enclosure. Liquid flow means are provided for introducing liquid to be sampled into the main enclosure. Sensing means are further provided for detecting a predetermined level of the liquid to be sampled introduced in the main enclosure. The sensing means is connected to control means to shut off the liquid flow means to cause a first volume of the liquid to be sampled to flow out of the enclosure. A sample collecting container is located in the main enclosure for receiving and containing a second volume of the liquid to be sampled. Means are further provided to remove the second volume of liquid to be sampled from the collecting container for analysis.

8 Claims, 4 Drawing Figures

SAMPLE COLLECTING SYSTEM

BACKGROUND OF THE INVENTION

1. Field of the Invention

The present invention relates to a sample collecting system in which an effluent is sampled at predetermined intervals for analysis.

2. Description of the Prior Art

In order to monitor the pollutants in plant effluents whereby to control them within an acceptable level, it is necessary to continuously sample the effluent. In view of strict pollution controls now imposed by various governments, it is necessary to provide records indicating the amount of pollutants contained in an effluent discharged into streams or rivers or even into settling reservoirs.

SUMMARY OF THE INVENTION

It is a feature of the present invention to provide a sample collecting system which is reliable, economical, automatic and capable of periodically obtaining a sample of an effluent whereby to provide samples for periodic analysis.

According to the above object, from a broad aspect, the present invention provides a sample collecting system comprising a main enclosure. Liquid flow means are provided for introducing liquid to be sampled into the main enclosure. Sensing means are further provided for detecting a predetermined level of the liquid to be sampled introduced in the main enclosure. The sensing means is connected to a control means to shut off the liquid flow means to cause a first volume of the liquid to be sampled to flow out of the enclosure. A sample collecting container is located in the main enclosure for receiving and containing a second volume of the liquid to be sampled. Means are further provided to remove the second volume of liquid to be sampled from the collecting container for analysis.

From a further broad aspect the present invention provides a method of extracting a liquid sample from a main liquid line and which comprises the steps of sensing the rate of flow of liquid in the main liquid line; directing liquid from the main liquid line to flow into a main container; sensing a predetermined level of the liquid in the main container and shutting off the flow into the main container, and collecting a sample of the liquid in the main container for analysis.

BRIEF DESCRIPTION OF THE DRAWINGS

A preferred embodiment of the present invention will now be described with reference to the accompanying drawings in which.

DESCRIPTION OF THE PREFERRED EMBODIMENTS

Figure 1:
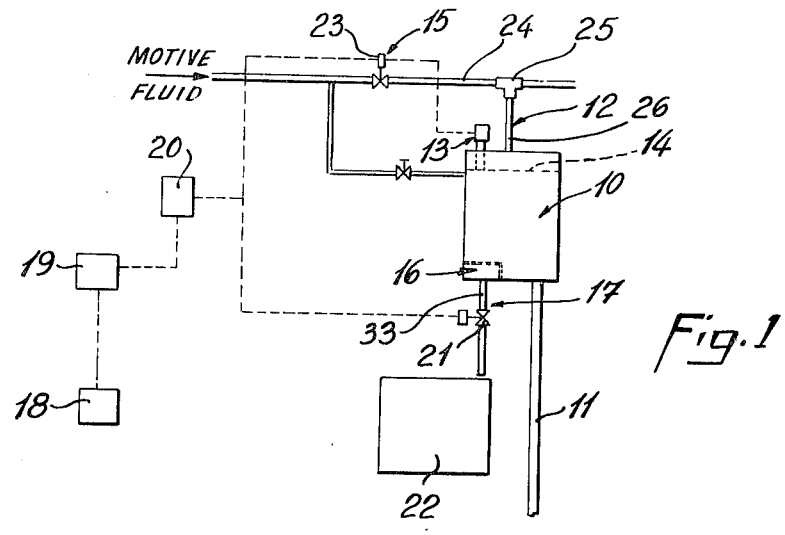
FIG. 1 is a schematic diagram illustrating a system of extracting a liquid sample from a main liquid line and utilizing the apparatus of the present invention.

Referring now to FIG. 1, there is shown the system of the present invention and comprising a main enclosure 10 which is connected to an effluent discharge line or channel (not shown) through a sample line 11. Liquid flow means 12 is connected to the main enclosure for introducing liquid to be sampled into the main enclosure 10 via the sample line 11. Sensing means 13 is connected to the main enclosure 10 for detecting a predetermined level 14 of the liquid to be sampled in the main enclosure. The sensing means 13 is connected to control means 15 to shut-off the liquid flow means 12 to cause a first volume (that indicated by liquid level 14) of the liquid to be sampled to flow out of the main enclosure 10. A sample collecting container 16 is provided in the main enclosure 10 and receives therein a second volume of the liquid to be sampled. Means 17 is further provided to remove the second volume of liquid to be sampled from the collecting container 16 for analysis.

As shown in FIG. 1, a flow transmitter 18, and a suitable flow sensing device (not shown), are mounted at a location upstream from the sample line 11. A recorder integrater device 19 is suitably mounted and connected to the flow transmitter to totalize the transmitted flow signal from the flow transmitter to cause a contact closure of a timer 20 after a predetermined flow total of the effluent. This contact closure initiates a sample cycle of the system.

At the beginning of each sample cycle, the means 17 to remove the second volume of liquid, herein shown as a dump valve 21, is opened momentarily to deposit the sample from the previous cycle into a holding tank 22 or any other suitable device, for further or immediate analysis of the sample. The control means 15, herein a solenoid valve 23, in then energized allowing motive water flow through the fluid line 24. An eductor 25 is connect in the fluid line 24 and to the main container 10 via conduit 26, to create a vacuum in the main container 10 to cause the effluent to be drawn up through the sample line 11 and into the main container 10. When the effluent in the main container 10 rises to the level 14 the sensing means 13, herein the level switch solenoid means 15 is deenergized. This de-energizing interrupts the flow motive fluid through the eductor by shutting off the solenoid in valve 23 and thus breaking the vacuum into the main container 10. Thus, the effluent in the main container 10 will drain through the sample line 11.

Figure 3:
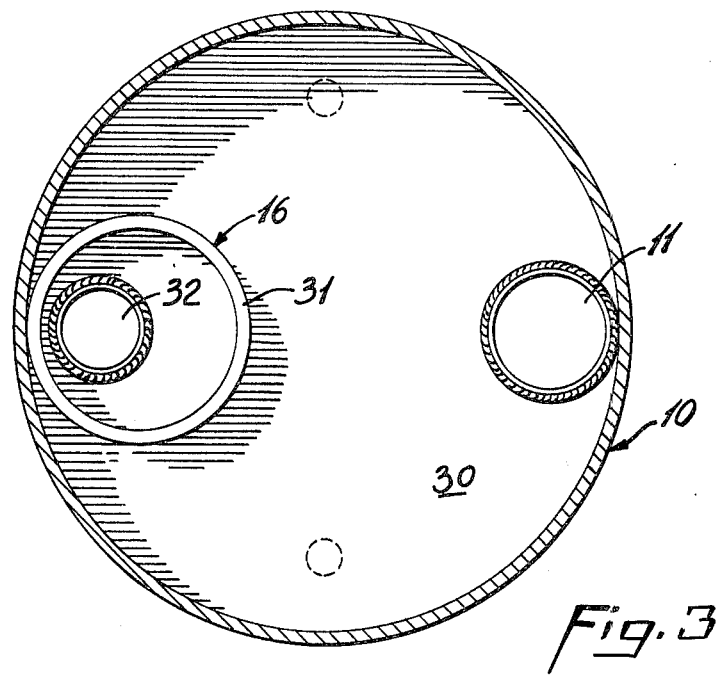
FIG. 3 is an end view along section lines 3—3 showing the bottom wall of the main enclosure.
Figure 4:
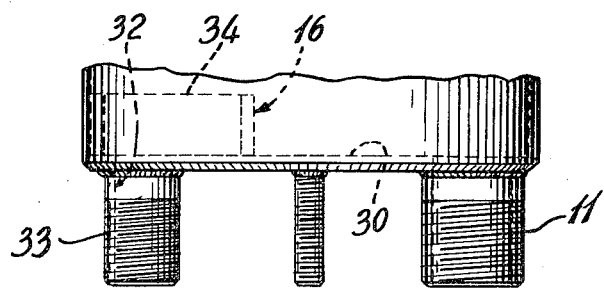
FIG. 4 is a fragmented side view of the bottom portion of the main enclosure.

As shown in FIGS. 3 and 4, the main container is a substantially cylindrical enclosure and having a bottom wall 30 with the sample line 11 opening into the bottom wall for inflow and outflow of the liquid to be sampled. The sample collecting container 16 is substantially a cylindrical cup having a vertically extending side-wall 31. An outlet port 32 is provided in the bottom wall 30 and surrounded by the sidewall 31 and having a conduit 33 with the dump valve or control valve 21 connected thereto. The area within the conduit 33 and the area within the sidewalls 31 define a second volume of the liquid to be sampled. As can be seen, the open upper end 34 of the collecting container 16 lies substantially below the predetermined level 14 whereby, when the effluent is removed from the main enclosure 10, the area within the sidewall 31 as well as in the conduit 33 above the valve 21, will be filled with that effluent liquid. After the liquid to be sampled is removed from the main enclosure the dump valve 21 is opened thus causing a predetermined volume of liquid, contained within the sample collecting container and part of conduit 33, to be removed therefrom for analysis.

Figure 2:
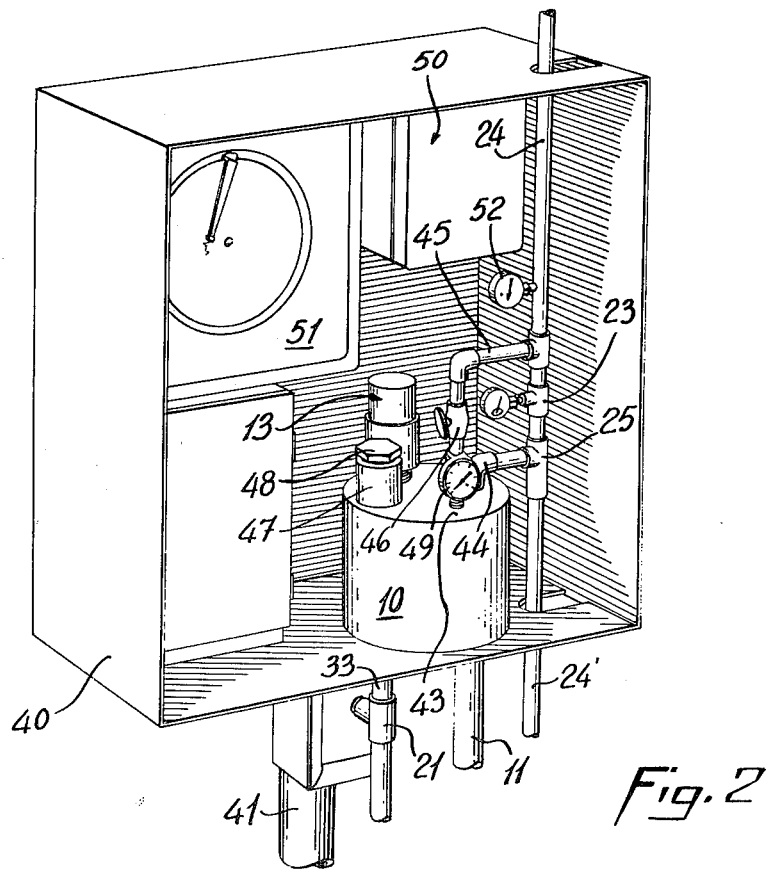
FIG. 2 is a perspective view of the system of the present invention.

Referring now to FIG. 2, the system is shown mounted in a housing 40. The housing is secured by suitable means herein a support frame 41 at a suitable test area. As herein shown the liquid flow means, herein a motive water line 24, is connected to the top wall 43 of the main enclosure 10 to a connector pipe 44 whereby to create a suction within the main enclosure to cause an effluent liquid to be drawn up through the sample line 11 and into the enclosure 10.

The solenoid valve 23 is herein shown connected upstream of the eductor 25. The purpose of the eductor 25 is to cause a suction in the pipeline 44 (see FIG. 2) or pipeline 12 (see FIG. 1) as water in the main line 24 flows through the eductor and towards the discharge end 24' of the water line 24. The line 24 could also be connected in the form of a loop for recirculating the water.

As shown in FIG. 2, a flushing conduit system 45 may also be provided and connected between the water line 24 upstream of the solenoid valve 23 and to the top wall 43 of the enclosure 10. This flushing line is provided for flushing the interior of the main enclosure 10 to clean it from any residual effluent whereby to remove impurities or traces of pollutants which may have been left in the enclosure from previous samples. A hand operable valve 46 is provided in the flushing conduit 45 to permit the water flow through the conduit and into the enclosure 10.

As illustrated in FIG. 2, an inspection port 47 having a closure plug 48 may be provided substantially above the sample collecting container 16 whereby to permit visual inspection of the interior of the main enclosure and particularly of the sample collecting container 16. A vacuum gauge 49 may also be provided on the top wall 43 of the main enclosure to monitor the vacuum therein. A further pressure gauge 52 may also be connected to the water line 24.

The operation of the sampling cycle may be controlled by a timer circuit 50 suitably mounted within the housing 40 whereby samples are automatically taken at regular time intervals throughout the day. The flow recorder 51 may also be provided within the housing 40 to meter the rate of flow of the effluent.

Thus, in operation it can be seen that the sample collecting system of the present invention consists in sensing the flow of an effluent in a main discharge line by means of a flow recorder 51 and periodically directing some of the liquid from the effluent line to flow into a main container 10 via a sample line 11. A predetermined level of the effluent is then sensed into the container 10 and the system is shut-off wherein the effluent is caused to flow out from the main enclosure 10 via the sample line 11 and back into the effluent line. However, a predetermined volume of the effluent is trapped within the sample collecting container 16 and this effluent is then discharged and collected for analysis. The system may be caused to operate either in relation to effluent flow rate or at specific time intervals.

With the system of the present invention as above described, it can be seen that an accurate monitor of the average effluent flow content can be had as it is made up of small samples taken at regular or period intervals throughout a period of time. Further, the system is designed to allow ease of installation and reliable maintenance-free performance. All components which are in contact with the effluent are made of corrosion resistant stainless steel or any other suitable material.

I claim:

1. A sample collecting system comprising a main sealed enclosure having a bottom wall, a conduit opening into said bottom wall for inflow and outflow of said liquid to be sampled, sensing means for detecting a predetermined level of said liquid to be sampled in said main enclosure, said sensing means being connected to control means to shut-off said liquid flow means to cause a first volume of said liquid to be sampled to flow out of said main enclosure, a sample collecting container in said main enclosure for receiving and containing a predetermined volume of said liquid to be sampled, said sample collecting container including a sidewall defining a containing area for said second volume and extending from said bottom wall, said collecting container having an open upper end positioned below said predetermined level, whereby said containing area is filled with said liquid within said main enclosure, and gravity means to remove said second volume of liquid to be sampled from said collecting container for analysis prior to introduction of further liquid into said main enclosure.

2. A sample collecting system, as claimed in claim 1, wherein said means to remove said second volume is an outlet port in said bottom wall and surrounded by said sidewall of said collecting container, and a conduit having a control valve connected to said outlet port for removal of said second volume of said liquid to be sampled.

3. A sample collecting system, as claimed in claim 1, wherein said liquid flow means comprises a suction device connected to said main enclosure for effecting a suction of a liquid to be sampled into said main enclosure.

4. A sample collecting system as claimed in claim 3, wherein said suction device includes a main fluid flow line, an eductor in said main fluid line and connected to a port in said main enclosure, and a valve in said fluid line upstream from said eductor for controlling the flow of fluid in said fluid line.

5. A sample collecting system, as claimed in claim 4 wherein said fluid flow line is a water flow line, a flushing conduit connected between said water line and said main enclosure for flushing said main enclosure, and a valve in said flushing conduit to close said flushing conduit.

6. A sample collecting system, as claimed in claim 1, wherein said sensing means is a level probe switch, said switch being connected to a valve whereby to cut-off said liquid flow means, said liquid flow means being a suction device connected to said main enclosure for effecting a suction of a liquid to be sampled into said main enclosure.

7. A sample collecting system, as claimed in claim 1, wherein a closeable inspection port is provided in a top wall of said main container and positioned to provide visual inspection of said sample collecting container.

8. A sample collecting system, as claimed in claim 1, wherein a flow sensing device is provided upstream in a sewer line from said liquid flow means, an integrator connected to said flow sensing device to operate said liquid flow means after a predetermined flow total has been detected by said sensing device.

* * * * *